Figure 1:
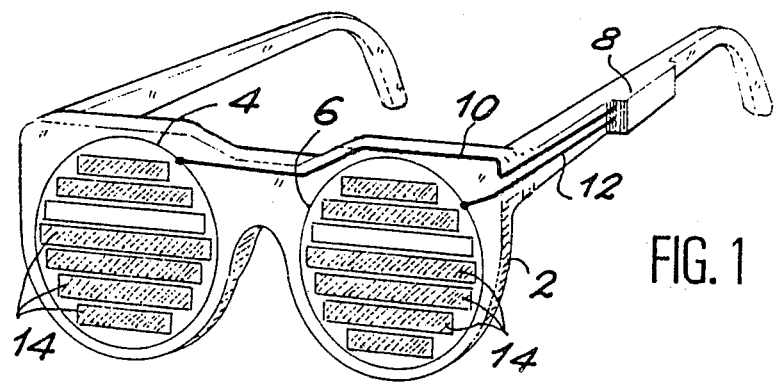

United States Patent [19]

Klein

[11] Patent Number: 4,842,400

[45] Date of Patent: Jun. 27, 1989

[54] VISUAL APPARATUS

[75] Inventor: Siegfried Klein, Paris, France

[73] Assignees: Commissariat a L'Energie Atomique; Siegfried Klein, both of Paris, France

[21] Appl. No.: 215,611

[22] Filed: Jul. 6, 1988

[30] Foreign Application Priority Data

Jul. 7, 1987 [FR] France .............................. 87 09642

[51] Int. Cl.⁴ .......................... G02C 1/00; G02C 7/10; G02C 7/16

[52] U.S. Cl. .................................... 351/158; 351/41; 351/44; 351/45; 350/331 R

[58] Field of Search .................... 351/41, 158, 44, 45; 350/331 R, 330, 332; 2/432, 433; 128/16.5

[56] References Cited

U.S. PATENT DOCUMENTS 4,012,129 3/1977 Byler .
4,462,661 7/1984 Witt .

FOREIGN PATENT DOCUMENTS

| 1131284 | 10/1968 | European Pat. Off. . |
| 852829 | 11/1939 | France . |
| 563709 | 1/1958 | France . |
| 1265417 | 6/1960 | France . |
| 1288617 | 6/1961 | France . |
| 2151623 | 4/1973 | France . |
| 2530039 | 1/1984 | France . |
| WO81/02795 | 10/1981 | PCT Int'l Appl. . |
| 2128362 | 4/1984 | United Kingdom . |
| 2170613 | 8/1986 | United Kingdom . |

Primary Examiner—Rodney B. Bovernick
Attorney, Agent, or Firm—Norman P. Soloway

[57] ABSTRACT

The visual apparatus makes it possible to limit the instantaneous luminous intensity without reducing the field of vision and comprises a plate with an opaque surface having a transparent slot, a support (2) on which said plate is mounted, said support bearing on part of the body of said person, said plate thus being placed in front of an eye of said person and a scanning means (8) connected to said plate for scanning the opaque surface of said plate by said transparent slot. The apparatus is used more particularly as medical spectacles in the case of cataracts, or as sunglasses.

14 Claims, 2 Drawing Sheets

VISUAL APPARATUS

DESCRIPTION

The present invention relates to a visual apparatus for limiting the instantaneous luminous intensity passing through the crystalline lens of the eye without reducing the visual field.

The invention more particularly relates to an application in the medical field for persons suffering with cataracts.

It also applies in all cases where a person is likely to be blinded by an excessive luminous intensity. It can therefore e.g. be used by a welder for providing protection against the luminous intensity emitted by a welding plasma or by a car driver for providing protection against the luminous intensity emitted by a car headlight.

It can also be used in sunglasses with the major advantage of not having to have recourse for reducing the luminous intensity to tinted lenses, which considerably modify the colouring of the real image.

Cataracts are an ailment of the eye consisting of decalcification between the facets of the eye's crystalline lens. This leads to a diffusion of the light passing through the crystalline lens, so that the vision is less clear, i.e. dim.

It is known that this ailment can be treated by surgery, but it develops slowly over a period of several years, so that patients suffering from it generally put up with this problem with an ever poorer vision and several years elapse before they have recourse to surgery.

For evaluating the degree of opacity of the crystalline lens, ophthalmologists often make use of a non-transparent disk with a small calibrated orifice. The field of vision of the eye is then considerably reduced, but at the same time the fraction of the image received by the retina through said orifice is infinitely clearer.

The improvement to the image perceived through this small orifice can easily be explained. Thus, when the crystalline lens suffers from a cataract, the light is partly diffused within the same before reaching the retina. For a given degree of decalcification, the magnitude of said diffusion is essentially dependent on two factors, being on the one hand the intensity of the lighting source and on the other the fraction of the crystalline lens traversed by said light. In other words, when the plate provided with a small orifice is placed in front of the eye, the light is only diffused in part of the crystalline lens, which clearly has the consequence of the total diffusion within the same being a function of the fraction of the illuminated crystalline lens volume. Therefore the diffusion is reduced and the image is clearer.

The invention aims at an apparatus intended more particuarly to improve the vision of a person suffering from a cataract.

The invention more particularly relates to a visual apparatus to be worn in front of the eyes of a person, characterized in that it comprises a plate having an opaque surface provided with a transparent slot, a support on which is mounted said plate, the support bearing on part of the body of said person, said plate being placed in front of the eye of said person and a scanning means connected to the plate for scanning the opaque surface of said plate by the said transparent slot.

Thus, the visual field is subdivided in time. The reduction of the luminous intensity is obtained by the slot moving through an appropriate scan. As in the cinema, during the displacement of said slot, the persistence of vision comes into effect and therefore the normal visual field of the eye is re-established.

The invention also relates to a visual apparatus like a pair of spectacles having two plates, each constituted by an opaque surface provided with a transparent slot.

In preferred manner, each plate is a cell having two transparent walls between which is arranged an optical material, whose transparency is electrically controllable, each cell having electrodes disposed on the inner faces of said transparent walls and defining controllable zones shaped like a slot, said electrodes receiving the electrical signals from the scanning means. The optical material can advantageously be a liquid crystal.

According to another advantageous embodiment, each plate is constituted by an opaque membrane having a slot-like orifice, the scanning means controlling the displacement of said slot by translation or rotation.

The characteristics and advantages of the invention can be better gathered from the following description given in an illustrative and non-limitative manner with reference to the attached drawings, wherein show:

FIG. 1 an embodiment of the invention in which the plates are constituted by liquid crystal cells.

Figure 2:
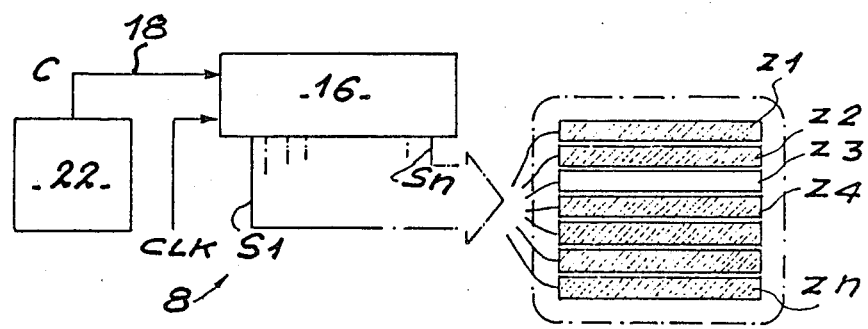

FIG. 2 diagrammatically an embdoiment of the scanning means of the apparatus of FIG. 1.

Figure 3A:
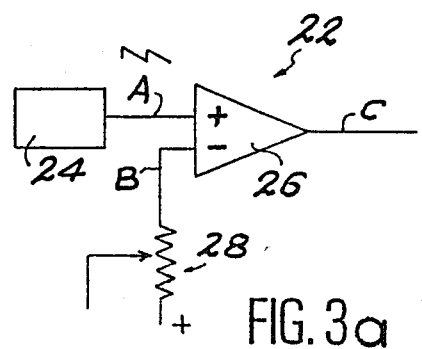

FIG. 3a diagrammatically an embodiment of the loading means 22 of the said scanning means.

Figure 3B:
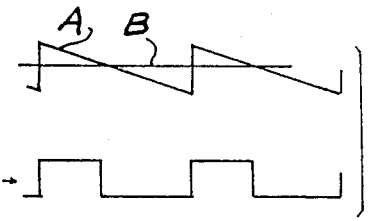

FIG. 3b the configuration of the signals produced by the loading means.

Figure 4:
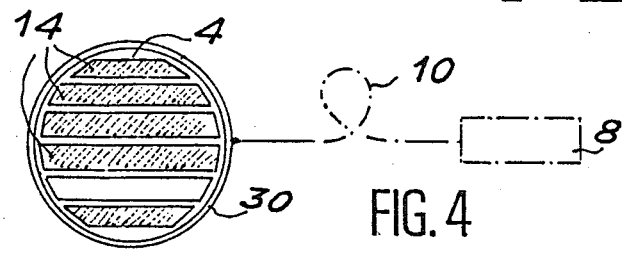

FIG. 4 an embodiment of the apparatus according to the invention having a single plate.

Figure 5:
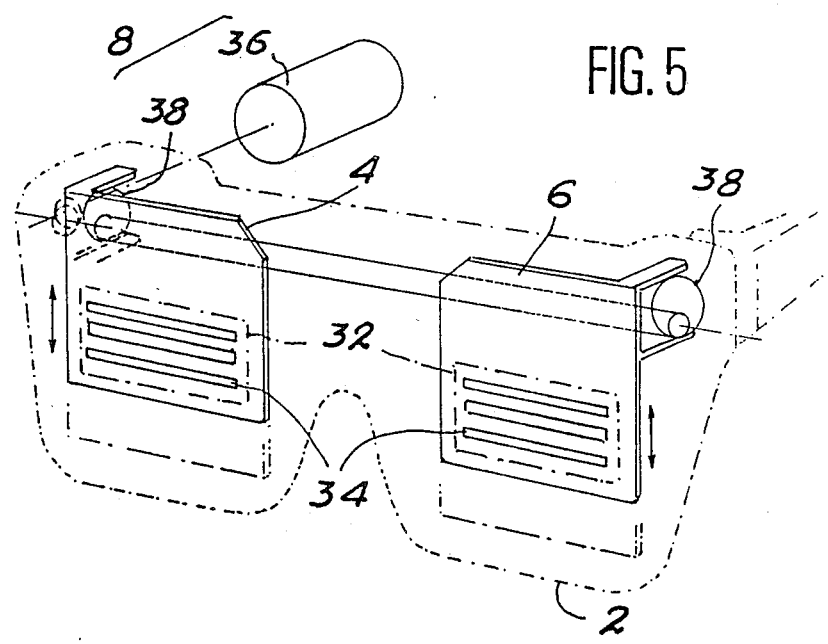

FIG. 5 an embodiment of the invention in which the slot is an orifice made in a membrane, the scanning means moving said slot in translation.

Figure 6:
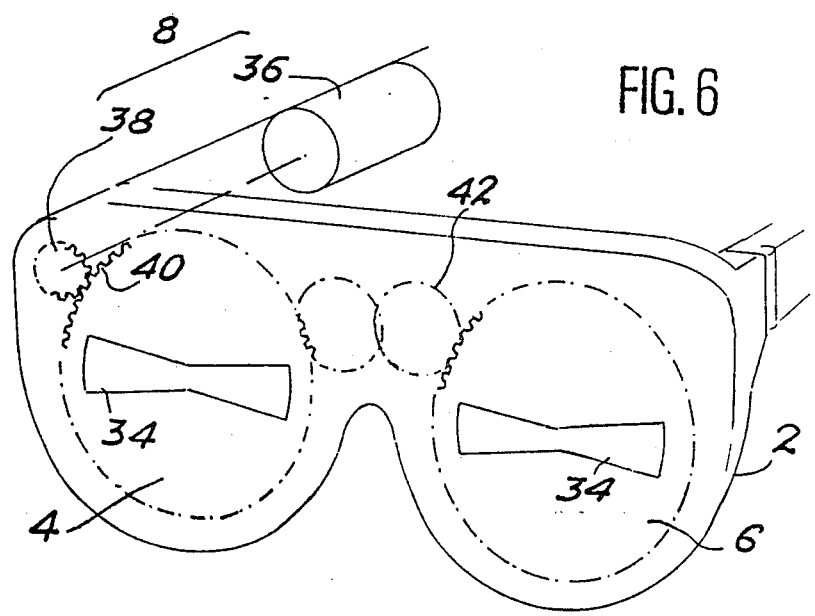

FIG. 6 an embodiment of the apparatus according to the invention in which the slot is constituted by an orifice in an opaque disk, the scanning means rotating said slot.

FIG. 1 shows a first embodiment of the apparatus according to the invention, which comprises a support 2, like a spectacle frame, two plates 4, 6 and a scanning means 8 having two control channels 10,12 respectively connected to the plates 4,6. Each plate is constituted by a liquid crystal cell having etched electrodes for defining independent strips. Conventionally each strip can be electrically controlled so as to be either transparent, or opaque.

In FIG. 1, each plate is in the form of a disk. However, it is obvious that this shape is not necessary and that each plate can e.g. be square or rectangular. In the same way, although the optically controllable zones are represented in the form of horizontal strips, the invention is not limited to this embodiment and in fact covers active zones having random shapes, such as e.g. circular sectors.

The scanning means 8 can be located on support 2, as shown in fig. 1. This is advantageous if the scanning means 8 is light and not very large. In the opposite case, the scanning means 8 can be fixed to the clothing of the patient or can be placed in a pocket. The scanning means 8 emits electrical signals on channels 10 and 12 for controlling in a conventional manner the transparent or opaque state of each zone 14 of each plate 4,6.

The electrical signals emitted by the scanning means 8 are chosen in such a way that a transparent zone constituted by one or more consecutive strip periodically scans the surface of plate 4, e.g. from top to bottom. An embodiment of said scanning means 8 is diagrammatically shown in FIG. 2.

Scanning means 8 essentially comprises a shift register 16 incorporating a series input 18 and n parallel outputs $S_1, \ldots, S_n$. The scanning means 8 also comprises a loading means 22 for loading a sequence of n bits into shift register 16. The loading means 22 enables the user to fix the width of said transparent slot. Said loading means 22 supplies a signal C constituted by a sequence of n bits, incorporating bits of value 1, followed by bits of value 0, the number of bits of value 1 determining the width of the transparent slot.

Each bit of the shift register 16 is associated with one of the zones $z_1, z_2, \ldots, z_n$ of a liquid crystal plate. The values of the bits emitted on outputs $S_1, \ldots, S_n$ of the shift register 16 determine the transparent or opaque state of the associated optical zone. For example, a bit of value 1 produces an electric voltage making transparent the associated optical zone. The scanning of the transparent slot constituted by one or more consecutive zones is obtained by a cyclic displacement of the bits of shift register 16 by means of a clock signal CLK. The frequency of said clock signal is chosen as a function of the number of strips n, in such a way that the plate scanning frequency is preferably in excess of 16 Hz which, taking account of the persistence of vision, makes said scan invisible.

FIG. 3a diagrammatically shows an embodiment of the loading means 22. It comprises a generator 24 for supplying a sawtooth signal A, a differential amplifier 26 having a positive input receiving the signal A and a negative input, a potentiometer 28, whose value is adjustable by the user for supplying a signal B on the inverting input of the differential amplifier 26. The signal C supplied by the differential amplifier 26 is applied to the series input 18 of the shift register 16 shown in FIG. 2.

FIG. 3b is a chronogram illustrating the configuration of signals A,B and C of the loading means 22. The amplitude of signal B is fixed by the user by means of potentiometer 28. Signal C is periodic and is of the same period as the signal A supplied by generator 24. At the start of each period, said signal C has a positive square-wave pulse, whose width is a function of the amplitude of signal B. This width determines the number of consecutive transparent zones of each plate.

The apparatus according to the invention shown in FIG. 1 has two plates 4,6, each constituted by a liquid crystal cell. Obviously, the apparatus according to the invention is not limited to the embodiment of the pair of spectacles type having two plates 4,6 and can instead also be applied to an apparatus of the monocle type having a single plate.

Such an apparatus is diagrammatically shown in FIG. 4. It comprises a plate 4 having a plurality of horizontal strips 14, whereof the transparent or opaque state is electrically controllable. This control is realized by the scanning means 8 with the aid of electric signals transmitted by a channel 10. The plate support 30 is here simply constituted by the circumference of the plate.

In each of the embodiments shown in FIGS. 1 and 4, the plates have a size of approximately 35 mm and have 10 segments, each with a width of 2 mm and separated from one another by gaps of approximately 0.20 mm. The liquid crystal is of the helical nematic type and is normally opaque, but becomes transparent under the effect of an electric voltage.

In the embodiment shown in FIGS. 1 and 4, the plates are constituted by liquid crystal cells, in which the scan of the slot is obtained without mechanical displacement. The apparatuses according to the invention shown in FIGS. 5 and 6, however, have a slot constituted by an orifice in an opaque membrane, which is moved in order to scan the slot.

According to a first embodiment shown in FIG. 5, the apparatus has a support 2 on which are fixed two opaque plates 4,6, each having a mobile opaque surface 32 provided with a slot 34. The scanning means 8 has a motor 36, which rotates the parts 38, the latter being associated with each plate 4,6, so as to produce a periodic vertical translation movement of the slots 34 of each of these plates.

FIG. 6 illustrates an embodiment in which the slot is rotatable. In the represented apparatus, the opaque plates 4 are constituted by disks and have in each case a slot 34 disposed in accordance with a diameter of said disk. For rotating plate 4, the circumference has a gear 40.

The scanning means 8 is constituted by a motor 36 and a toothed wheel 38, which is rotated by motor 36 and rotates plate 4. A gear means 42 is also located between plate 4 and plate 6, so as to transmit the rotary movement of the first plate to the second plate.

The apparatus according to the invention leads to a significant improvement in the vision of persons suffering from cataracts as a result of the weak instantaneous field of vision. The total field of vision of the eye is scanned by moving the slot at a frequency preferably exceeding 16 Hz. This scan is not perceived due to the persistence of vision.

The apparatus according to the invention is of interest for persons suffering from cataracts, because the process makes it possible to significantly reduce the diffusion of light passing through a crystalline lens with a cataract and therefore improves the vision of persons suffering from this ailment.

It can also be used with advantage for persons liable to be exposed to an excessive luminous intensity for the eye. This is particularly the case with welders, who must be protected against the luminous intensity created by the welding plasma. This also applies to car drivers, who can be blinded at night by the headlights of an oncoming vehicle.

It can also be used in the form of sunglasses with the major advantage of reducing the luminous intensity, without having to have recourse to tinted lenses, which considerably modify the colouring of the real image.

In all cases, the apparatus according to the invention makes it possible to reduce the intensity of the luminous radiation received without reducing the field of vision.

I claim:

1. Visual apparatus to be worn in front of the eyes of a person, characterized in that it comprises a plate having an opaque surface provided with a transparent slot, a support (2) on which is mounted said plate, the support bearing on part of the body of said person, said plate being placed in front of the eye of said person and a scanning means (8) connected to the plate for scanning the opaque surface of said plate by the said transparent slot.

2. Apparatus according to claim 1, characterized in that the visual apparatus comprises another plate (6) having an opaque surface provided with a transparent slot, said other plate being mounted on said support so that it is located in front of the other eye of said person, said scanning means being connected to said other plate for scanning the surface of said other plate by said transparent slot.

3. Apparatus according to claim 1, characterized in that each plate is a cell constituted by two transparent walls between which is arranged an optical material, whose transparency is electrically controllable, each cell having electrodes disposed on the inner faces of the transparent walls defining controllable zones (14) shaped like a slot, said electrodes receiving electrical signals from said scanning means.

4. Apparatus according to claim 3, characterized in that the optical material is a liquid crystal film.

5. Apparatus according to claim 1, characterized in that each plate (4,6) is an opaque disk provided with a slot (34) following a diameter of the disk and the scanning means (8) controls the rotation of the disk.

6. Apparatus according to claim 1, characterized in that each plate is substantially rectangular, the opaque surface being formed by a membrane (32) having a slot (34) and the scanning means (8) controls the translation of the membrane.

7. Apparatus according to claim 1, characterized in that said support is a spectacle frame.

8. Apparatus according to claim 1, characterized in that the scanning frequency of the opaque surface by the transparent slot is fixed by the scanning means (8) at a frequency exceeding 16 Hz.

9. Apparatus according to claim 2, characterized in that each plate is a cell constituted by two transparent walls between which is arranged an optical material, whose transparency is electrically controllable, each cell having electrodes disposed on the inner faces of the transparent walls defining controllable zones (14) shaped like a slot, said electrodes receiving electrical signals from said scanning means.

10. Apparatus according to claim 9, characterized in that the optical material is a liquid crystal film.

11. Apparatus according to claim 2, characterized in that each plate (4,6) is an opaque disk provided with a slot (34) following a diameter of the disk and the scanning means (8) controls the rotation of the disk.

12. Apparatus according to claim 2, characterized in that each plate is substantially rectangular, the opaque surface being formed by a membrane (32) having a slot (34) and the scanning means (8) controls the translation of the membrane.

13. Apparatus according to claim 2, characterized in that said support is a spectacle frame.

14. Apparatus according to claim 2, characterized in that the scanning frequency of the opaque surface by the transparent slot is fixed by the scanning means (8) at a frequency exceeding 16 Hz.

* * * * *